United States Patent [19]
Faust et al.

[11] 4,101,384
[45] Jul. 18, 1978

[54] APPARATUS FOR THE FERMENTATIVE CONVERSION OF A NUTRIENT MIXTURE BY MEANS OF MICROORGANISMS

[75] Inventors: Uwe Faust, Fischbach; Rudolf Knecht, Dortmund-Aplerbeck; Wolfgang Lautenschlager, Wersau; Wilhelm Wengeler, Bochum-Stiepel, all of Fed. Rep. of Germany

[73] Assignee: Friedrich Uhde GmbH, Dortmund, Fed. Rep. of Germany

[21] Appl. No.: 652,534

[22] Filed: Jan. 26, 1976

Related U.S. Application Data

[62] Division of Ser. No. 629,098, Nov. 5, 1975, abandoned.

[30] Foreign Application Priority Data

Nov. 16, 1974 [DE] Fed. Rep. of Germany ....... 2454443

[51] Int. Cl.² .............................................. C12B 1/16
[52] U.S. Cl. ..................................... 195/142; 261/92; 195/143; 366/328

[58] Field of Search ................ 195/142, 143; 259/109; 261/92

[56] References Cited

U.S. PATENT DOCUMENTS

| | | | |
|---|---|---|---|
| 2,997,424 | 8/1961 | Mayer | 195/143 |
| 3,460,810 | 8/1969 | Mueller | 195/143 |
| 3,660,244 | 5/1972 | Che | 195/143 |

*Primary Examiner*—Alvin E. Tanenholtz
*Attorney, Agent, or Firm*—Malcolm W. Fraser

[57] ABSTRACT

An apparatus for the fermentative conversion of a nutrient mixture by means of microorganisms in the presence of a gas containing oxygen. The nutrient mixture and gas are mixed to yield a phase state with a relative density of less than 0.3 referred to water. The process is carried out in a closed reaction vessel having inlet and outlet pipes for the nutrient mixture, its components and the product. The vessel is also provided with inlet and outlet pipes for the oxygen-bearing gas. A paddle wheel within the vessel provides the distribution device.

1 Claim, 4 Drawing Figures

APPARATUS FOR THE FERMENTATIVE CONVERSION OF A NUTRIENT MIXTURE BY MEANS OF MICROORGANISMS

This is a division, of application, Ser. No. 629,098 filed Nov. 5, 1975 now abandoned.

BACKGROUND OF THE INVENTION

The invention concerns an apparatus for the fermentative conversion of a nutrient mixture by means of microorganisms in the presence of a gas containing oxygen. Apparatuses of this sort are employed in the production of proteins.

It is necessary, with such processes, to attain a highly effective oxygen input into the nutrient mixture since a corresponding reduction of capital expenditure/operational costs as compared with the amount of protein obtained may then be attained. As is known, microorganisms are employed in processes for the fermentative conversion of nutrient mixture that in their aqueous phase have a water content of 90% or more. The amount of oxygen necessary for the fermentative transformation is added in the form of air. The fermentation process is essentially dependent on the distribution, that is to say the rotation and mixing of all reactants and their diffusion through the phase interfaces. An effort is made to hold or to attain a high transfer rate. In fermentation, a definite temperature must be maintained as the optimum growth temperature.

Nutrient mixtures contain the elements necessary for the production of proteins, the elements being in the form of chemical compounds that are either water soluble, emulsible or dispersive.

As a source of carbon, the following may be used:
methanol
ethanol
paraffins
gas oil
methane
glucose and other sugars
starch
cellulose As a source of nitrogen:
$NH_3$
$HNO_3$ and its salts
urea
hydrazine The following inorganic substrates can be added to the nutrient mixtures:
$H_3PO_4$
$H_2SO_4$
NaOH and their salts
KOH
$Ca(OH)_2$ In addition, the following trace elements are added to the nutrient mixture:
$MgSO_4$
$FeSO_4$
and/or $ZnSO_4$ The following micoorganisms are used:
Bacteria of the following typical strains:
micrococcus
pseudomanas
chrombacterium
flavobacterium
as well as yeasts of families such as
hansenula
torulopsis
candida There are processes known in which air is introduced by a distribution system into the nutrient mixture in aqueous phase and this aerated mixture is further vigorously mixed by an agitator.

Fermentation processes take place in so-called fermenters. These are large vessels or columns, the greatest part of whose contents is aqueous nutrient. The fermentation, assisted by microorganisms, is carried out by the so-called submerged culture with the addition of air or oxygen. The thorough intermixing of the reaction components is effected mechanically by stirrers, pneumatically by air disbrbution or in loop reactors with aeration by jets or tubes or via the so-called airlift fermenters or, hydrodynamically with the aid of packing material.

Fermentation in the conventional stirred tanks takes place in a satisfactory manner as far as product quality and growth characteristics are concerned. The expenditure of energy is, of course, considerable since a large part of the energy fed into the stirring apparatus is transferred to the vessel walls in the form of heat, without having been used for the process.

Fermentation in the various types of airlift fermenters have a much more favorable exploitation of energy but they only have a sufficient utilization of oxygen when they attain a certain height, approx. 20 m. or more.

Fermentation in loop reactors with nozzles and tube gasification has positive results and is satisfactory in comparison with other known types of fermenters. Circulation rates of a 100 times per hour and more are attained. Problems arise when foaming occurs at high protein concentrations, resulting in occasional work stoppages.

SUMMARY OF THE INVENTION

The invention proposes to solve the problem of finding a process in which a high mass transfer rate is attained between the aqueous phase of the nutrient mixture and the air as oxygen carrier, while avoiding disadvantages of other known processes.

The invention effectively solves this problem in that the nutrient mixture and the gas are mixed to yield a phase state with a relative density of less than 0.3 referred to water.

A closed reaction vessel serves to carry out the process according to the invention. It has inlet and outlet pipes for the nutrient mixture, its components and the product, inlet and outlet pipes for the oxygen-bearing gas and at least one horizontally arranged driving shaft which carries the distribution device, a sort of paddle wheel, mounted perpendicularly to the shaft. An essential part of this invention is that the individual reactants of the fermentative process, in particular microorganisms, water, dissolved nutrient salts and substrates are distributed in the reactor space in the form of aerosols. On the one hand this produces very large surfaces, and on the other, it restricts to a small area the diffusion distance to and from the places of biochemical conversion. The very large surfaces, i.e. the face interfaces, are a precondition for good mass transfer rates and simultaneously the attainment of a protein concentration beyond known values.

The particular advantages of this invention as compared with conventional processes and with otherwise identical boundary conditions, such as nutrient solution composition, fermentation temperature, pH value, air throughput and microorganisms, are a considerably higher energy-specific productivity, higher oxygen yield, and a higher final concentration, as can be seen from the example.

The process can be carried out batchwise as well as in continuous operation. The speed of the paddle wheel should be so adjusted as to distribute almost completely the mixture in the gas space, the mixture then being in suspension without being excessively turbulent.

BRIEF DESCRIPTION OF DRAWINGS

A preferred embodiment of the invention is shown on the accompanying drawings in which.

DESCRIPTION OF PREFERRED EMBODIMENT

In the following example, operational data and results of a conventional fermentative conversion process and those of a process according to this invention are compared. A fermentation with candida yeast (candida lipolytica) and n-paraffin ($C_{10}$–$C_{14}$ cut) is carried out under the conditions given in the table and in the apparatus shown in FIGS. 3 and 4.

| Fermenter type | mixing vessel | | paddle-wheel fermenter |
| --- | --- | --- | --- |
| volume: | 20 l | | 16 l |
| Composition of nutrient solution: | $(NH_4)_2SO_4$ | 0.53% | |
| | $Na_2HPO_4 \cdot 12H_2O$ | 0.2 % | |
| | $KH_2PO_4$ | 0.4 % | |
| | $MgSO_4 \cdot 7H_2O$ | 0.02% | |
| | KCl | 0.02% | |
| | dry yeast | 0.05% | |
| | sterilized drinking water | | sterilized |
| Addition of paraffin: | carbon limited, automatic | | |
| Fermentation temperature: | 30° | | 30° |
| pH value: | from 6.5 falling to 3.8, then constant through automatic additon of $NH_3$ | | |
| speed: | 1,500 rpm | | 75 rpm |
| power consumption: | 20 kW/m³ | | 7.5 kW/m³ |
| air throughput (gas/water, min.): | 1.0 vol/vol, min. | | 0.3–2.0 vol/vol, min. |
| Results: | | | |
| energy-specific productivity: | 35 g/kWh | | 1,300 g/kWh |
| oxygen yield: | 10% | | 50% |
| final concentration attained: | 2.0% | | 4.5% |

Doubling time at a biomass concentration in the fermenter:

| 1 | % BC | 5 h | 3.5 h |
| --- | --- | --- | --- |
| 1.5 | % BC | 11 h | 3.5 h |
| 2 | % BC | 20 h | 3.5 h |
| 3 | % BC | 00 | 3.5 h |
| 5 | % BC | 00 | 20 h |

As can be seen from the smaller air throughput, the loss of water and substrate with exhaust air is only half as great as when the mixing vessel is being used.

Figure 1:
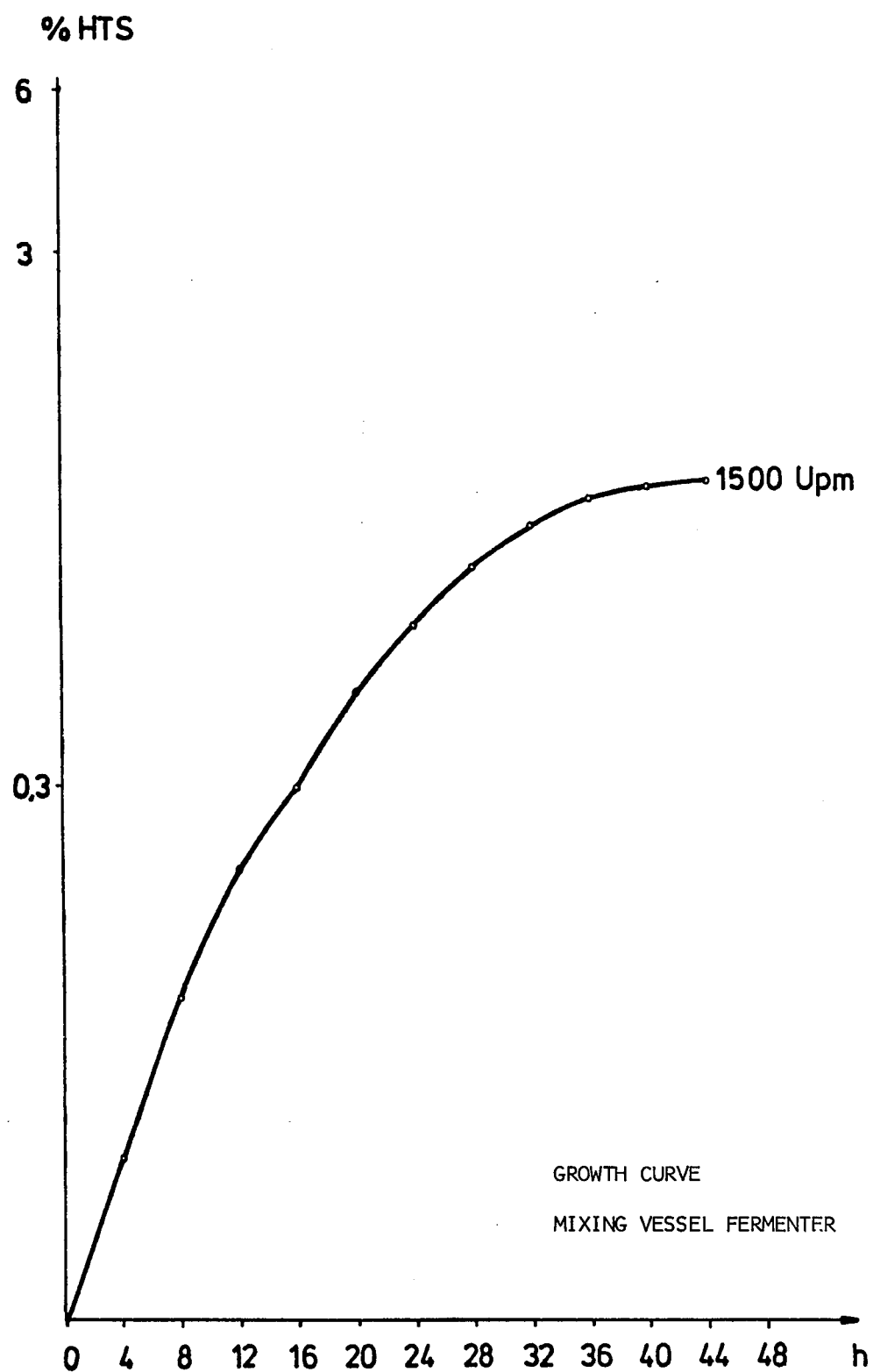
FIG. 1 shows a growth curve in a conventional stirred tank.
Figure 2:
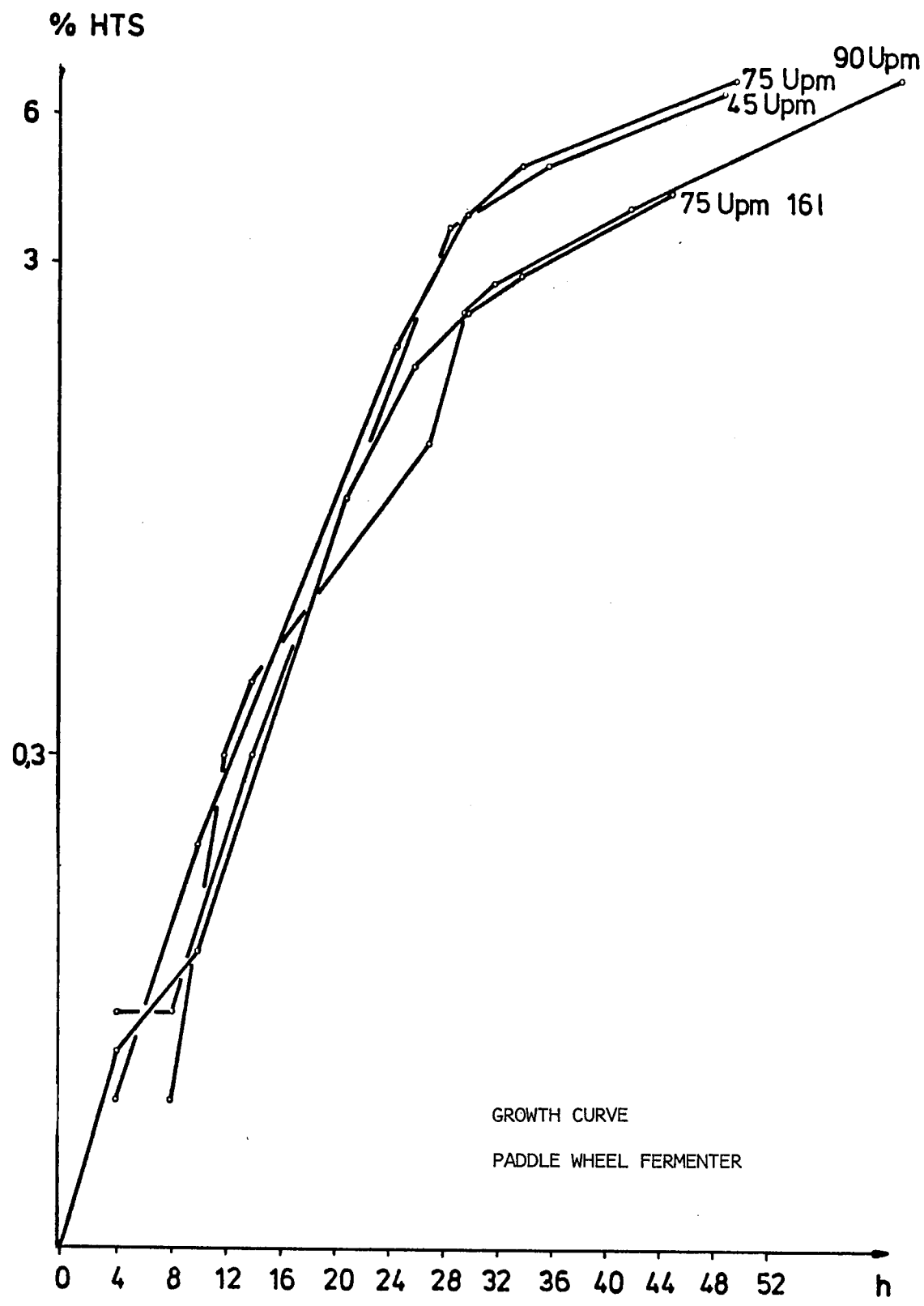
FIG. 2 shows a growth curve employing the process in accordance with this invention.

The growth curve in a conventional stirred tank with comparable dimensions and identical control system and mode of operation, in accordance with the above example, is shown on FIG. 1. For comparison, the growth curve using the process herein before described according to this invention, is shown on FIG. 2. An example of the apparatus according to the invention for carrying out the process is shown on FIGS. 3 and 4 and will now be described in detail.

Figure 3:
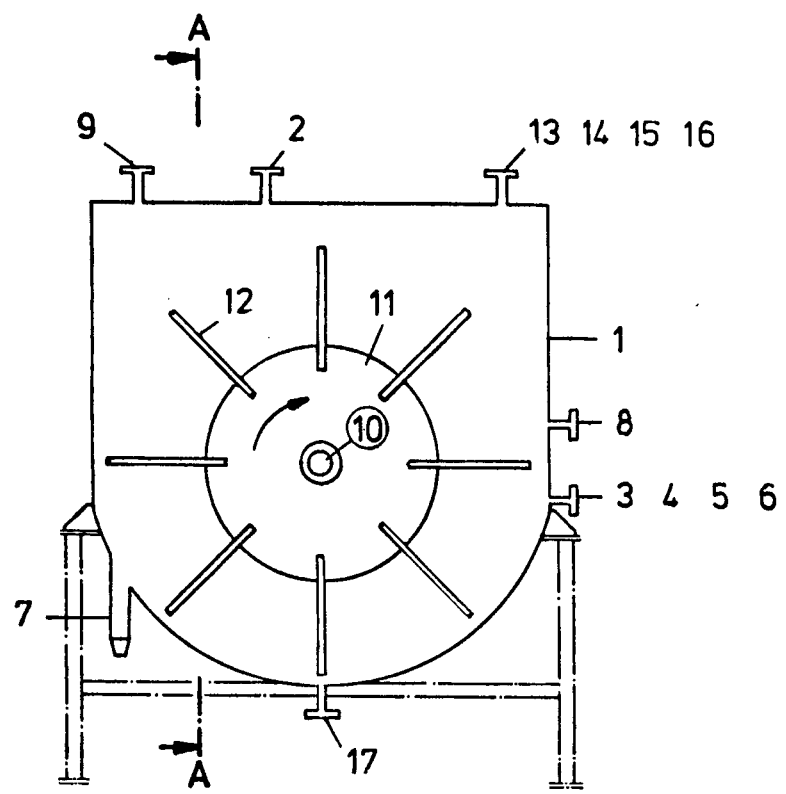
FIG. 3 is a diagrammatic view in side elevation of an apparatus for carrying out the process.

The form shown in FIG. 3 consists of a closed reaction vessel 1 with necessary inlet and outlet nozzles 2, 3, 4, 5, and 6, and 7 respectively for substrate, nutrient solution, reflux water, $NH_3$ water for fermentation broth and microorganisms. Nozzles 8 and 9 are provided for the inlet and outlet respectively of air or other oxygen-bearing gas. In addition, the reactor vessel has a turnable horizontal shaft 10, which is provided with discs or webs 11 on which paddles 12 that distribute the fermentation medium, are attached. Only a small gap is provided between the outer ends of the paddles and the vessel wall. The paddles 12 can be disposed radially or at an angle of ± 20° to the axis of the discs 11. To complete FIG. 3, a series of nozzles 13 through 16 are necessary for measuring purposes and a nozzle 17 is necessary for emptying the vessel, these being shown or indicated.

Figure 4:
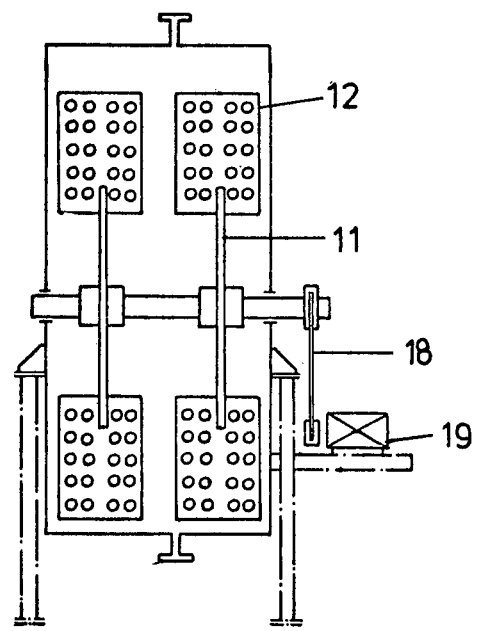
FIG. 4 is a vertical sectional elevation on the line A—A of FIG. 3.

In FIG. 4, the arrangement of paddle wheels 12 on the shaft 10 can be seen. The shaft 10 is driven by a motor 19 through a reduction drive 18. Holes or slits are formed in the paddles 12 and serve to produce a better turbulence.

What we claim is:

1. Apparatus for carrying out a fermentative conversion of a nutrient mixture by means of microorganisms in the presence of an oxygen bearing gas consisting of:
    (a) a closed reaction vessel provided with six inlet and outlet nozzles for the nutrient mixture, its components and the product,
    (b) input and output pipes for said vessel for an oxygen-bearing gas,
    (c) a horizontally disposed shaft within said vessel,
    (d) motors means to drive said shaft, and
    (e) a distributing device in the form of 2 paddle wheels each consisting of a circular disc and 8 flat paddles each of which has five rows of four holes evenly spaced thereon with each paddle equally spaced from each other and arranged radially on the disc and perpendicular to the axis of the disc, arranged on said shaft so that each disc is perpendicular to the axis of said shaft and the axis of the said shaft passes through the center of each disc and the discs are so spaced that the paddles attached to the outer periphery of one disc do not touch the paddles attached to the outer periphery of another disc and wherein the paddle wheels are so arranged that a small gap is provided between the outer end of each paddle wheel and the wall of the reactor vessel.

* * * * *